United States Patent [19]

Hamill et al.

[11] Patent Number: 4,885,170

[45] Date of Patent: Dec. 5, 1989

[54] ANTIBIOTIC A80509

[75] Inventors: Robert L. Hamill, Greenwood; Raymond C. Yao, Carmel, both of Ind.

[73] Assignee: Eli Lilly and Company, Indianapolis, Ind.

[21] Appl. No.: 172,677

[22] Filed: Mar. 24, 1988

[51] Int. Cl.$^4$ .......................... A61K 35/74; C12P 1/06
[52] U.S. Cl. ...................................... 424/117; 435/169
[58] Field of Search .......................... 424/117; 435/169

*Primary Examiner*—Jerome D. Goldberg
*Attorney, Agent, or Firm*—Nancy J. Harrison; Leroy Whitaker

[57] ABSTRACT

New antibiotic A80509, its $C_1$–$C_7$-alkyl ester derivatives and salts are useful antibacterial and anticoccidial agents and improve feed efficiency and growth in animals. Methods of making A80509 by fermentation of, and a biologically pure culture of, *Streptomyces mutabilis* NRRL 18269 are also provided.

9 Claims, 2 Drawing Sheets

ANTIBIOTIC A80509

SUMMARY OF THE INVENTION

This invention relates to a new antibiotic designated A80509 and to a process for producing A80509 by culturing a strain of *Streptomyces mutabilis*, NRRL 18269, under submerged aerobic fermentation conditions until a substantial level of the antibiotic is produced. A80509 can be isolated by separating the broth from the mycelium and extracting the broth with polar organic solvents. A80509 can be further separated and purified by adsorption techniques such as column chromatography.

Because *S. mutabilis* NRRL 18269 is a newly discovered strain, this invention further provides a biologically pure culture of this microorganism.

Antibiotic A80509 has antibacterial and anticoccidial activity, but it is especially useful because it improves feed efficiency and weight gains in animals. For example, this effect has been demonstrated in ruminants and poultry. Thus, this invention also provides methods and compositions pertaining to the use of A80509 to improve weight gains and feed efficiency in animals.

DETAILED DESCRIPTION OF THE INVENTION

Improved antibiotics continue to be needed in the veterinary field. Enhancing growth promotion in animals is one desired feature of such antibiotics. Growth promotion can be achieved by reducing disease, increasing weight gains or increasing feed efficiency.

A80509 is a new antibiotic of unknown structure. A80509 contains a tripeptide group (Cys-Ala-Ile) and a chlorosalicylic acid moiety.

Characteristics of A80509

Figure 1:
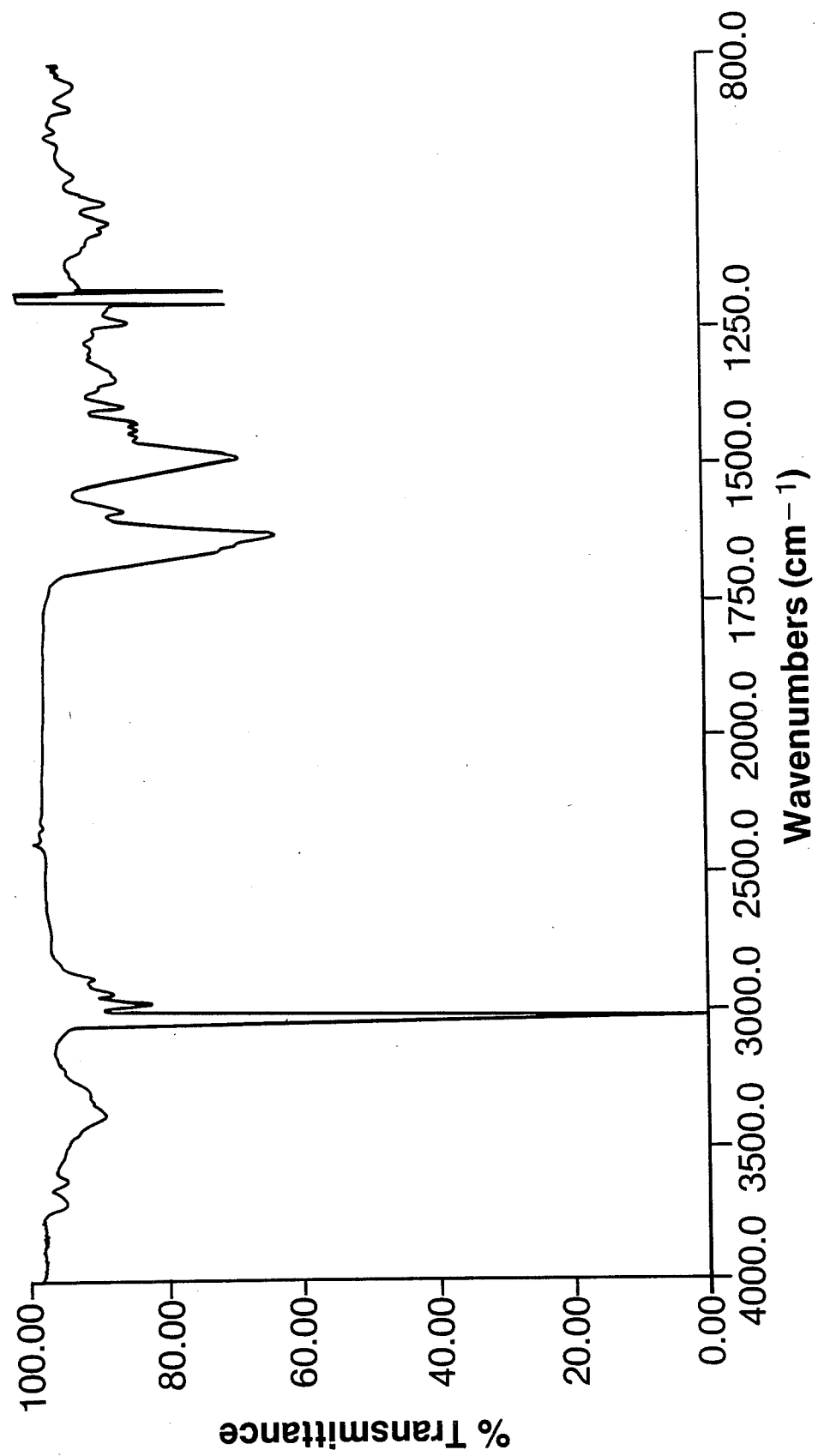
FIG. 1 shows the infrared (IR) absorption spectrum of A80509 (free acid) in chloroform.
Figure 2:
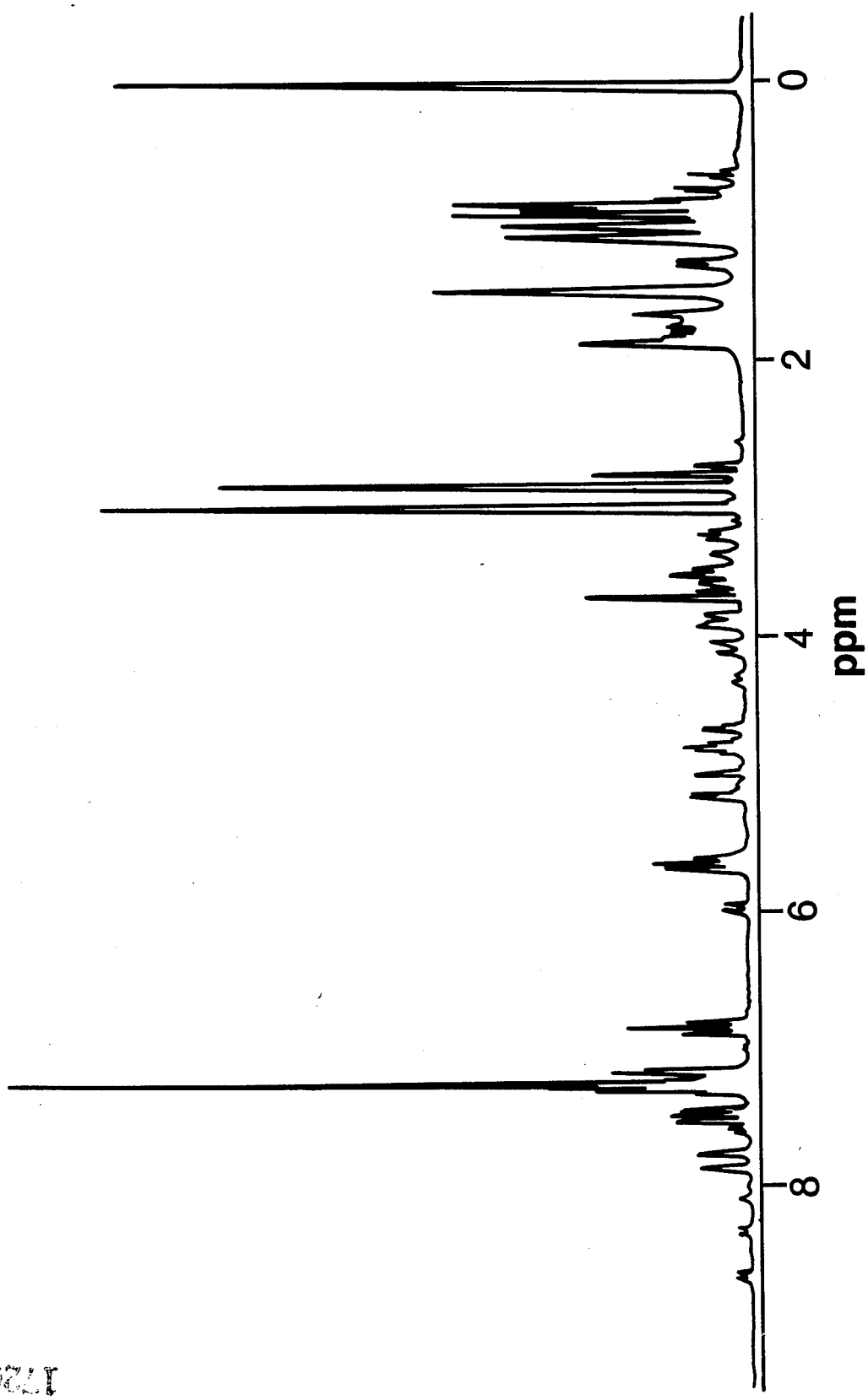
FIG. 2 shows the proton nuclear magnetic resonance (NMR) spectrum of A80509 (free acid) in $CDCl_3$.

Antibiotic A80509 has the following characteristics:
State: white amorphous powder (lyophilized)
Mp: 147°–148° C.
pKa: =6.7 (66% aqueous dimethylformamide)
$[\alpha]^{25}D: +35.1°$ (c 10, MeOH)
Mol. wt.: 856 (field desorption and fast atom bombardment mass spectrometry)
Empirical formula: $C_{42}H_{57}N_6O_9ClS$ UV (ETOH): 336 nm ($\epsilon$5,070); acidic–241 ($\epsilon$12,600) and 311 ($\epsilon$4,750)
IR ($CHCl_3$) FIG. 1; shows absorption at the following frequencies ($cm^{-1}$): 3032, 2972, 1660, 1644, 1601, 1504, 1468, 1454, 1440, 1413, 1365, 1262, and 1226.

| Elemental Analysis: | | |
|---|---|---|
| | Calcd | Found |
| C | 58.9 | 59.04 |
| H | 6.71 | 6.98 |
| N | 9.81 | 9.93 |
| O | 16.81 | 17.02 |
| Cl | 4.02 | 4.10 |
| S | 3.74 | 3.96 |

Solubility: Insoluble in water; soluble in lower alcohols such as methanol, ketones such as acetone, esters such as ethyl acetate, halogenated hydrocarbons such as chloroform and hydrocarbons such as diethyl ether, benzene, toluene and warm hexane.

Amino-acid analysis: indicates the present of cysteine (1), alanine (1) and isoleucine (1).

A80509 has an acid function capable of forming salts and ester derivatives. The alkyl ester derivatives and pharmaceutically acceptable salts of A80509 are also useful as antibiotics and as agents which increase weight gains and feed efficiency in animals.

The term "alkyl" means a $C_1$ to $C_7$ straight or branched chain hydrocarbon, preferably a $C_1$ to $C_4$ hydrocarbon, e.g., methyl, ethyl, propyl, isopropyl, n-butyl, etc.

The salts and ester derivatives of A80509 are useful for separating and purifying the antibiotic. The pharmaceutically acceptable salts are particularly useful. Examples of salts are the alkali-metal, alkaline-earth-metal and amine salts of A80509.

Representative and suitable alkali-metal and alkaline-earth metal salts of A80509 include the sodium, potassium, lithium, cesium, rubidium, barium, calcium and magnesium salts. Suitable amine salts of A80509 include the ammonium and the primary, secondary, and tertiary $C_1$–$C_4$-alkylammonium and hydroxy-$C_2$–$C_4$-alkylammonium salts. Illustrative amine salts include those formed by reaction of A80509 with ammonium hydroxide, methylamine, sec-butyamine, isopropylamine, diethylamine, di-isopropylamine, ethanolamine, triethylamine, 3-amino-1-propanol and the like.

When treating an animal, it is not ordinarily of great significance whether the free base or a salt of a compound is used. A salt form may, however, be chosen for reasons of economy, convenience or toxicity.

Antibiotic A80509 is produced by culturing an A80509-producing strain of *Streptomyces mutabilis* under submerged aerobic conditions in a suitable culture medium until substantial antibiotic activity is produced. The antibiotic is recovered using various isolation and purification procedures understood in the art.

A culture of the A80509-producing organism has been deposited and made part of the stock culture collection of the Northern Regional Research Center, Agricultural Research, North Central Region, 1815 North University St., Peoria, Ill., 61604, from which it is available to the public under the accession number NRRL 18269.

For convenience, the new microorganism of this invention, which produces antibiotic A80509, is called culture A80509. Culture A80509 was isolated from a soil sample from Spain.

Frederick P. Mertz of the Lilly Research Laboratories carried out taxonomic studies of the A80509 culture. Based on these studies, the new organism is classified a new strain of *Streptomyces mutabilis* (Preobrazhenskaya and Ryabora 1957) Pridham, Hesseltine and Benedict 1958 [V. B. D. Skerman, V. McGowan, and P. H. A. Sneath, eds., "Approved Lists of Bacterial Names," *Int. J. Syst. Bacteriol* 30:225–420 (1980)]. This classification is based on a literature comparison [E. B. Shirling and D. Gottlieb, "Cooperative Description of Type Cultures of *Streptomyces*. II. Species Descriptions from First Study," *Int. J. Syst. Bacteriol.* 18:69–189 (1968)]. Simultaneous laboratory comparisons between A80509 and the type strain of *S. mutabilis* were considered unnecessary.

Methods Used

The methods recommended by the International Streptomyces Project (ISP) [E. B. Shirling and D. Gottlieb, "Methods for Characterization of Streptomyces Species," *Int. J. Syst. Bacteriol.* 16:313-340 (1966)] for the characterization of Streptomyces species were followed.

ICSS-NBS Centroid Color Charts, standard sample No. 2106 (National Bureau of Standards, 1958, U.S. Department of Commerce, Washington, D.C.) and the Color Harmony Manual (4th ed., Container Corporation of America, Chicago, Ill., 1958) were used to assign color names to the reverse side and to aerial spore mass, respectively.

Morphology was studied using an optical light microscope. A scanning electron microscope (SEM) was used to study the spore surface ornamentation.

Melanoid pigment production (chromogenicity) was determined with ISP No. 1 (tryptone-yeast extract broth), ISP No. 6 (peptone-yeast extract iron agar) and No. 7 (tyrosine agar).

The isomers of diaminopimelic acid (DAP) and the carbohydrates in hydrolysates of whole cells were established by the chromatographic methods of Becker et al. [B. Becker, M. P. Lechevalier, R. E. Gordon, and H. A. Lechevalier, "Rapid Differentiation between Nocardia and Streptomyces by Paper Chromatography of Whole-cell Hydrolysates," *Appl. Microbiol.* 12:421-423 (1964)] and of Lechevalier and Lechevalier [M. P. Lechevalier and H. Lechevalier, "Chemical Composition as a Criterion in the Classification of Aerobic Actinomycetes," *Int. J. Syst. Bacteriol.* 20:435-443 (1970)]

Resistance to antibiotics was measured by padding antibiotic sensitivity discs onto the surface of seeded ISP No. 2 agar plates.

Starch hydrolysis was determined by testing for the presence of starch with iodine on ISP No. 4 (inorganic salts-starch agar) plates.

Cultural Characteristics

Culture A80509 grew on a number of complex and defined media; however, there were as many media on which it had poor or no growth. Only two media, oatmeal agar (ISP media 3) and potato carrot agar (PC), supported more than a trace of aerial hyphae.

The aerial spore mass was white; the reverse color was yellowish white to yellowish gray. The culture did not produce soluble pigments. The cultural characteristics are summarized in Table I.

TABLE I

Cultural Characteristics of A80509 on Various Agar Media[a]

| Medium | Characteristics | Medium | Characteristics |
|---|---|---|---|
| ISP 2 | G: Poor<br>R: 72.d.OY<br>Am: None<br>Sp: None | Czapek's | G: Good<br>R: 93.y Gray<br>Am: Trace: a White<br>Sp: None |
| ISP 3 | G: Fair<br>R: 92.y White<br>Am: Fair: a White<br>Sp: None | Tomato Paste Oatmeal Agar | G: No growth<br>R: -<br>Am: -<br>Sp: - |
| ISP 4 | G: Abundant<br>R: 93.y Gray<br>Am: Trace(edges): White<br>Sp: None | Potato Carrot Agar | G: Good<br>R: 92.y White<br>Am: Good: a White<br>Sp: None |
| ISP 5 | G: Abundant<br>R: 92.y Gray<br>Am: Trace(edges): White<br>Sp: None | Jensen's Agar | G: Good<br>R: 92.y White<br>Am: None<br>Sp: None |
| ISP 7 | G: Good<br>R: 76.1.yBr<br>Am: None<br>Sp: Light-brown | Glucose Asparagine | G: Poor<br>R: 92.y White<br>Am: None<br>Sp: None |
| ATCC No. 172 | G: Good<br>R: 92.y White<br>Am: None<br>Sp: None | Glycerol Glycine | G: No growth<br>R: -<br>Am: -<br>Sp: - |
| Tap Water Agar | G: No growth<br>R: -<br>Am: -<br>Sp: - | Yeast Dextrose Agar | G: Poor<br>R: 93.y Gray<br>Am: None<br>Sp: None |
| Emerson's Agar | G: Poor<br>R: 93.y Gray<br>Am: None<br>Sp: None | | |

[a]Incubated at 30° C. for 18 days
[b]G = growth;
R = reverse;
Am = aerial mycelium;
Sp = soluble pigment.

Morphological Characteristics

Culture A80509 produced an extensive substrate mycelium. Aerial hyphae were infrequently produced. When present, they formed short loops and hooks characteristic of Retinaculum-apertum (RA) morphology. Spirals were also observed. The spores were elliptical, had a smooth surface, and averaged 1.2×0.7 μm in size.

Physiological Characteristics

Culture A80509 utilized the following carbohydrates: cellobiose, D-fructose, D-galactose, glucose, glycerol, glycogen, i-inositol, D-lactose, D-maltose, D-mannitol, D-mannose, D-melizitose, D-melibiose, L-rhamnose, D-ribose, sucrose, D-trehalose and D-xylose. It was unable to utilize adonitol, D-arabinose, L-arabinose, cellulose, dextrin, dulcitol, ethanol, i-erythritol, inulin, α-methyl-D-glucoside, D-raffinose, salicin, sorbitol, L-sorbose, xylitol and sodium butyrate.

Culture A80509 grew in a temperature range of 10°-30° C. An optimal growth temperature appeared to be ~25° C. The culture had a mucoid consistency when grown on ISP medium No. 2.

Culture A80509 hydrolyzed starch and produced catalase. It did not reduce nitrate or produce melanoid pigments.

Culture A80509 was resistant to: cephalothin (30 μg), lincomycin (2 μg), oleandomycin (15 μg) and penicillin G (10 units). It was sensitive to: bacitracin (10 units), gentamicin (10 μg), neomycin (30 μg), rifampin (5 μg), streptomycin (10 μg), tetracycline (30 μg), tobramycin (10 μg) and vancomycin (30 μg).

Culture A80509 was extremely sensitive to NaCl. It was unable to grow in the presence of 1% levels of NaCl.

Cell-Wall Analysis

Hydrolyzed whole cells of A80509 contained LL-diaminopimelic acid, glucose and ribose. A80509 has, therefore, a type I cell wall and an N.C. sugar pattern (Lechevalier and Lechevalier, supra).

Identity of Culture A80509

The chemotaxonomic properties and general cultural and morphological characteristics of the A80509 culture support assignment of this strain to the genus Streptomyces. A literature comparison with similar strains indicates that A80509 should be classified as a strain of *Streptomyces mutabilis* (Preobrazhenskaya and Ryabova 1958) Pridham, Hesseltine and Benedict 1958 (Shriling and Gottlieb, supra). *S. mutabilis* is listed in the approved Lists of Bacterial Names (Skerman et al., supra) and is, therefore, a validly published species.

Table II summarizes a comparison between the published characteristics of *S. mutabilis* and A80509. The comparison shows agreement in every characteristic except utilization of arabinose.

TABLE II

| Comparison of A80509 and *S. mutabilis* | | |
|---|---|---|
| Characteristic | A80509 | *S. mutabilis* |
| Aerial spore color | White | White |
| Reverse side color | Non-distinctive | Non-distinctive |
| Morphology | RA | RA |
| Spore-chain length | 3–10μ | 3–10μ |
| Spore surface | Smooth | Smooth |
| Spore shape | Elliptical | Elliptical |
| Melanoid pigments | — | — |
| Carbon utilization: | | |
| glucose | + | + |
| arabinose | − | + |
| xylose | + | + |
| inositol | + | + |
| mannitol | + | + |
| fructose | + | + |
| rhamnose | + | + |
| sucrose | + | + |
| raffinose | − | − |
| galactose | + | + |
| salicin | − | − |

As is the case with other organisms, the characteristics of the A80509-producing culture of this invention, *Streptomyces mutabilis* NRRL 18269, are subject to variation. Spontaneous or induced mutants of the strain may be obtained by methods in the art. For example, mutants can be obtained by treatment with various known physical and chemical mutagens such as ultraviolet light, X rays, gamma rays and chemicals such as N-methyl-N'-nitro-N-nitrosoguanidine. Spontaneous and induced mutants of *Streptomyces mutabil* NRRL 18269 which retain the characteristic of A80509 production are considered part of this invention.

The culture medium used to grow the *Streptomyces mutabilis* cultures can be any one of a number of media. For economy in production, optimal yield, and ease of product isolation, however, certain culture media are preferred. Thus, for example, preferred carbon sources for large-scale fermentation include glucose, soluble starch and glycerol, although potato dextrin and the like can also be used.

Preferred nitrogen sources are soybean flour and yeast, although enzyme-hydrolyzed casein, meat peptones and the like can also be used.

Among the nutrient inorganic salts which can be incorporated in the culture media are the customary soluble salts capable of yielding zinc, sodium, magnesium, calcium, ammonium, chloride, carbonate, sulfate, nitrate and like ions.

Essential trace elements necessary for the growth and development of the organism should also be included in the culture medium. Such trace elements commonly occur as impurities in other substituents of the medium in amounts sufficient to meet the growth requirements of the organism. Foaming is not usually a problem, but small amounts (i.e. 0.2 mL/L) of an antifoam agent such as polypropylene glycol may be added to large scale fermentation media if needed.

For production of substantial quantities of antibiotic A80509, submerged aerobic fermentation in tanks is preferred. Small quantities of A80509 may be obtained by shake-flask culture. Because of the time lag in antibiotic production commonly associated with inoculation of large tanks with the spore form of the organism, it is preferable to use a vegetative inoculum. The vegetative inoculum is prepared by inoculating a small volume of culture medium with the spore form or mycelial fragments of the organism to obtain a fresh, actively growing culture of the organism. The vegetative inoculum is then transferred to a larger tank. The vegetative inoculum medium can be the same as that used for larger fermentations, but other media are also suitable.

A80509 is produced by the A80509-producing organism when grown at temperatures between about 25° and about 35° C. An optimum temperature for A80509 production appears to be about 30° C.

As is customary in submerged aerobic culture processes, sterile air is blown into the vessel from the bottom while the medium is stirred with conventional turbine impellers. During the fermentation, the level of dissolved oxygen should be maintained above 30% of saturation.

Production of antibiotic A80509 can be followed during the fermentation by testing samples of the broth for antibiotic activity against organisms known to be sensitive to the antibiotic. One assay organism useful in testing A80509 is *Bacillus subtilis* ATCC 6633. The bioassay is conveniently performed by the agar-well plate test.

Following its production under submerged aerobic fermentation conditions, A80509 can be recovered from the fermentation medium by methods used in the fermentation art. The antibiotic activity produced during fermentation of the A80509-producing organism occurs mainly in the filtered broth. Maximum recovery of A80509 is accomplished, therefore, by initially filtering the medium to separate the broth from the mycelial mass. The filtered broth can then be purified separately to give A80509.

A variety of techniques may be used separating and purifying A80509. One technique for separating A80509 from the filtered broth involves adjusting the broth to a pH of about 3–9 and extracting it with a suitable solvent such as, for example, ethyl acetate. Since extration at pH 3 or pH 7 leads to bad emulsions, a pH of about 9 is preferred for this procedure. The extracting solvent ca then be evaporated under to give A80509. A80509 can be further purified by adsorption procedures. A preferred procedure involves the use of silica gel chromatography.

Alternatively, the culture solids, including medium constituents and mycelium can be used without extraction or separation, but preferably after removal of water, as a source of A80509. For example, after production of A80509, the whole fermentation broth can be dried by lyophilization, by drum-drying, or by azeotropic distillation and drying. The dried broth is then mixed directly into feed premix.

The alkali-metal and alkaline-earth-metal cationic salts of A80509 are prepared according to procedures commonly used for the preparation of cationic salts. For example, the free acid of A80509 is dissolved in a suitable solvent such as acetone; a ½ volume of water is added; and this solution is adjusted to a pH of about 9 to 10 with the base of the desired cationic salt (e.g. NaOH, KOH). The salt thus formed can be isolated by routine methods, such as filtration or evaporation of the solvent.

One method of forming salts is to dissolve A80509 (acid form) in a water-immiscible solvent such as ethyl acetate, add an equal volume of water, and adjust the mixture to pH 10 with the corresponding cationic base (e.g. NaOH, KOH, etc.) The separated organic phase is washed with water and concentrated to dryness to give the desired salt.

Salts can also be formed by suspending A80509 in water, adding a sufficient amount of the desired base to dissolve the A80509 completely (pH 9.5 for NaOH, pH 10 for NH*OH), and freeze-drying to give the desired salt.

The salts formed with organic amines can be prepared similarly. For example, the gaseous or liquid amine can be added to a solution of A80509 in a suitable solvent such as acetone; the solvent and excess amine can be removed by evaporation.

A80509 alkyl ester derivatives are prepared by esterifying of the carboxyl group, using standard procedures.

A80509 and its salts and alkyl ester derivatives (A80509 compounds) have antibacterial and anticoccidial activity. A80509 compounds are especially active against anaerobic bacteria. The minimal inhibitory concentrations (MIC's) at which A80509 inhibits various bacteria, as determined by standard agar-dilution assays, are summarized in Tables III and IV. End points were read after 24-hour incubation.

TABLE III

| Antibacterial Activity of A80509 | |
|---|---|
| Test Organism | MIC (mcg/mL) |
| Streptococcus pyogenes C203 | 8 |
| Streptococcus pneumoniae Park 1 | 1 |
| Streptococcus faecalis X66 | 32 |
| Streptococcus faecalis 2041 | 32 |

TABLE III-continued

| Antibacterial Activity of A80509 | |
|---|---|
| Test Organism | MIC (mcg/mL) |
| Staphylococcus aureus X1.1 | >128 |
| Staphylococcus aureus V41 | >128 |
| Staphylococcus aureus X400 | >128 |
| Staphylococcus aureus S13E | >128 |
| Staphylococcus epidermidis Epi 1 | >128 |
| Staphylococcus epidermidis 222 | >128 |
| Hemophilis influenzae C.L. | >128 |
| Hemophilius influenzae 76 | >128 |
| Gram-negative bacteria tested | >128 |

TABLE IV

| Susceptibility of Anaerobic Bacterial Isolates to A80509 | |
|---|---|
| Anaerobic Bacteria | MIC (mcg/mL) |
| Clostridium difficile 2994 | 8 |
| Clostridium perfringens 81 | 8 |
| Clostridium septicum 1128 | >128 |
| Eubacterium aerofaciens 1235 | 8 |
| Peptococcus asaccharolyticus 1302 | <0.06 |
| Peptococcus prevoti 1281 | >128 |
| Peptostreptococcus anaerobius 1428 | >128 |
| Peptostreptococcus intermedius 1624 | 2 |
| Propionibacterium acnes 79 | 4 |
| Bacteroides fragilis 111 | 0.25 |
| Bacteroides fragilis 1877 | 16 |
| Bacteroides fragilis 1936B | 0.125 |
| Bacteroides thetaiotaomicron 1438 | ≦0.06 |
| Bacteroides melaninogenicus 1856/28 | ≦0.06 |
| Bacteroides melaninogenicus 2736 | >128 |
| Bacteroides vulgatis 1211 | ≦0.06 |
| Bacteroides corrodens 1874 | 0.25 |
| Fusobacterium symbiosum 1470 | >128 |
| Fusobacterium necrophorum 6054A | ≦0.06 |

Anticoccidial activity is another property of the A80509 compounds. In an in vitro tissue culture screen vs. *Eimeria tenella*, A80509 exhibited activity at 5 and 1 mcg/mL levels, but not at 0.2 mcg/mL. A80509 is relatively nontoxic. When administered to mice by the intraperitoneal route, A80509 had an $LD_{50}$ of >300 mg/kg.

An important property of the A80509 compounds is their ability to improve weight gains and feed efficiency in animals.

Studies have demonstrated that A80509 has a positive effect on weight gains in monogastric animals, such as poultry, and in ruminants.

For example, in a battery study, 7-day-old chicks (5 chicks each in 5 pens) were fed a rye-based diet in which A80509 (free base) was incorporated at a level of 20 g/ton for 7 days. This group was compared with a similar group of control chicks fed only the diet. The chicks receiving A80509 had an average weight gain of 279 g, whereas the control chicks had an average gain of 229 g. Thus, A80509 gave a 21.8% improvement in weight gain.

The A80509-treated chicks had a feed/gain ratio of 1.630, compared to 1.805 for that of the controls. Thus, A80509 improved the feed/gain ratio by 9.7%.

Another aspect of this ability of the A80509 compounds to improve feed-utilization efficiency in animals is that A80509 has useful protein-sparing activity.

Dietary protein in the rumen is rapidly hydrolyzed to free amino acids that are subsequently deaminated to ammonia and keto acids. Certain rumen bacteria take up the $NH_3$ and the carbon skeleton and resynthesize amino acids intracellularly. This procedure is accomplished at the expense of energy and nitrogen because not all the ammonia nitrogen is returned into amino acids. The loss of nitrogen via this mechanism, in addition to the varying degree of microbial protein digestibility, suggests that if plant protein could bypass rumen degradation, the animal could better utilize protein. Improved protein utilization should lead to increased growth and improved lactation.

A80509's protein-sparing activity is via its ability to inhibit deaminase, thereby blocking the breakdown from amino acids to ammonia and keto acids. A80509 is an effective deaminase inhibitor at levels as low as 1 ppm. A80509 inhibited 50% of the deaminase activity in in vitro rumen and monogastric screens. Thus, A80509 should improve efficiency of protein utilization in growing beef cattle and lactating dairy cattle and might also increase wool growth in sheep.

The methods for improving weight gains and feed efficiency in animals of this invention comprise administering an effective amount of an A80509 compound to the animal, preferably orally on a daily basis. Although a variety of factors must be considered in determining an appropriate concentration of A80509 compound, the rates of administration for improving weight gains and feed efficiency in poultry are generally in the range of about 2 to about 150 ppm in the feed and are preferably in the range of about 5 to about 75 ppm of feed ration.

The A80509 compounds are typically effective in inhibiting deaminase and, thereby, the efficiency of feed utilization when administered to ruminants orally at rates of from about 0.2 mg/kg/day to about 3 mg/kg/day. Preferable rates of administration are from about 0.5 mg/kg/day to about 1 mg/kg/day.

In another aspect, this invention relates to compositions for improving weight gains and feed efficiency in animals, such as ruminants and monogastric animals, comprising an effective amount of an A80509 compound for improving weight gains or improving feed efficiency together with a suitable vehicle. These compositions generally comprise feed ration and from about 25 to 200 grams per ton of an A80509 compound.

The A80509 compounds can be administered to animals orally or parenterally. They can also be administered by insufflation, i.e. by blowing the antibiotic, in the form of a medicated dust, into an enclosed space or room wherein the animals or poultry are held. The animals or poultry breathe the medicated dust present in the air; the medicated dust also is taken into the body through the eyes (a process called intraocular injection).

The most practical way to administer the A80509 compounds is by formulation into the feed supply. A variety of feeds, including the common dry feeds, liquid feeds, and pelleted feeds, may be used. Although the preferred method of administration is by mixing it with the animals' feed, it can also be administered in other ways, for example, tablets, drenches, boluses, or capsules. Each individual dosage unit should contain a quantity of A80509 compound directly related to the proper daily dose for the animal to be treated.

The methods of formulating drugs into animal feeds are well known. A preferred method is to make a concentrated drug premix which in turn is used to prepare medicated feeds. Typical premixes may contain from about 1 to about 200 grams of drug per pound of premix. Premixes may be either liquid of solid preparations.

The final formulation of feeds for animals or poultry will depend upon the amount of drug to be administered. The common methods of formulating, and pelleting feeds may be used to prepare feeds containing an A80509 compound.

The A80509 compounds may be formulated for parenteral administration by methods recognized in the veterinary pharmaceutical art. Effective injectable compositions containing the A80509 compounds may be in either suspension or solution form. In the solution form, the A80509 compound is dissolved in a physiologically acceptable carrier. Such carriers comprise a suitable solvent, preservatives such as benzyl alcohol, if needed, and buffers. Useful solvents include, for example, alcohols, glycols, or inert oils such as vegetable oils or highly refined mineral oils.

Injectable suspension compositions are prepared using a nonsolvent for the compound with adjuvants, as a carrier. The nonsolvent can be, for example, water or a glycol such as polyethylene glycol.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful for suspending the compounds. Lecithin, alkylphenol polyethylene oxide adducts, naphthalenesulfonates, alkylbenzenesulfonates, and the polyoxyethylene sorbitan esters are useful suspending agents in liquid nonsolvents.

Many substances which affect the hydrophilicity, density, and surface tension of the nonsolvent can assist in making injectable suspensions in individual cases. For example, silicone antifoams, glycols, sorbitol, and sugars can be useful suspending agents.

In the preparation of dusts or powders for administration by insufflation, the compounds are typically mixed with talc, diatomaceous earth, or some other inert substance as an adjuvant.

In order to illustrate more fully the operation of this invention, the following non-limiting examples are provided:

Example 1

Preparation of A80509

A. Shake-flask Fermentation of A80509

The culture *Streptomyces mutabilis* NRRL 18269, either as a lyophilized pellet or as a suspension maintained in liquid nitrogen, is used to inoculate a vegetative medium having the following composition:

| VEGETATIVE MEDIUM | |
|---|---|
| Ingredient | Amount (g/L) |
| Glucose | 10.0 |
| Soluble starch | 20.0 |
| Yeast extract | 5.0 |
| Enzymatic hydrolysate of casein* | 5.0 |
| CaCO$_3$ | 1.0 |
| Deionized water | q.s. 1 liter |
| Adjust the pH of the medium to about 7.2 before sterilizing. | |

*NZ Amine A, Sheffield Chemical Co., Norwich, N.Y.

Slants or plates are prepared by adding 2.5% agar to the vegetative medium. The inoculated slant is incubated at 30° C. for from about 10 to about 14 days. The mature slant culture is scraped with a sterile tool to loosen the spores and remove and mascerate the mycelial mat. About one-fourth of the loosened spores and culture growth thus obtained is used to inoculate 50 mL of a first-stage vegetation medium.

The inoculated first-stage medium is incubated in a 250-mL Erlenmeyer flask at 30° C. for about 48 hours on a shaker orbiting in a two-inch (5.08 cm) circle at 250 rpm.

This incubated first-stage medium (0.4 mL) is used to inoculate 50 mL of a production medium having the following composition:

| PRODUCTION MEDIUM | |
|---|---|
| Ingredient | Amount (g/L) |
| Glucose | 5.0 |
| Glycerol | 30.0 |
| Soybean Flour | 15.0 |
| Yeast Extract | 5.0 |
| $NH_4H_2PO_4$ | 0.7 |
| $MgSO_4 \cdot 7H_2O$ | 0.5 |
| NaCl | 3.5 |
| $CaCO_3$ | 3.0 |
| $K_2HPO_4$ | 1.0 |
| Cold tap water | q.s. 1 liter |

The inoculated production medium is incubated in a 250-mL wide-mouth Erlenmeyer flask at 30°–32° C. for 3 to 4 days on a shaker orbiting in a two-inch circle at 250 rpm.

B Tank Fermentation of A80509

In order to provide a larger volume of inoculum, 10 mL of incubated first-stage medium, prepared as described in Section A, is used to inoculate 400 mL of a second-stage growth medium having the same composition as that of the first-stage medium. This second-stage vegetative medium is incubated in a two-liter wide-mouth Erlenmeyer flask for about 54 hours at 30° C. on a shaker orbiting in a two-inch circle at 250 rpm.

Incubated second-stage vegetative medium (800 mL) thus prepared is used to inoculate 100 liters of sterile production medium, prepared as described in Section A, except that an antifoam agent or agents are added.

The inoculated production medium is allowed to ferment in a 165-liter stirred fermentation tank for 3 to 5 days at a temperature of about 30° C. Low airflow (0.25 v/v/m) and low rpm (50–300) in the stirred vessel maintain a dissolved oxygen level at about 60% of air saturation.

EXAMPLE 2

Isolation of A80509

Whole fermentation broth (100 L), obtained as described in Example 1, was adjusted to pH 9.0 with 5N NaOH and then extracted twice with ethyl acetate (56 L each) by stirring the mixture for one hour and decanting the ethyl acetate layer. The extracts were combined and concentrated in vacuo to a volume of 150 mL.

This concentrate was mixed with 200 mL of silica gel (Woelm, 70–140 mesh), and the mixture was dried in vacuo. The silica gel preparation was applied to a 7−×57-cm glass column containing 2.1 L of silica gel (Woelm, 100–200 μm), packed in toluene. The column was washed sequentially with toluene (3 L) and toluene:ethyl acetate (1:1, 3 L) collecting 1-L fractions.

Elution was followed by bioassay using *Bacillus subtilis*. A80509 was eluted with ethyl acetate. The fractions richest in A80509 were combined and concentrated to a residue.

The residue was dissolved in MeOH (10 mL) and applied to a 2.5−×65-cm stainless-steel column containing silica gel/$C_{18}$ (Whatman LP-1 silica gel/$C_{18}$) equilibrated in acetonitrile:water (65:35). The column was developed with acetonitrile:water (65:35) under pressure at a flow rate of 10 mL/min., collecting 20-mL fractions. Elution was monitored with a UV detector at 254 nm. Fractions richest in A80509 were identified by analytical HPLC, combined and concentrated to a residue. The residue was dissolved in dioxane and lyophilized to give 755 mg of A80509.

Other closely related fractions were combined and concentrated to a residue which was dissolved in dioxane and freeze-dried to give 1.011 g of semi-purified A80509. The semi-purified A80509 was rechromatographed on silica gel/$C_{18}$ by the method described supra to give an additional 880 mg of purified A80509 (total=1.635 g).

EXAMPLE 3

Alternate Preparation of A80509

Whole fermentation broth (4500 L), prepared as described in Example 1, was filtered through a filter press with the aid of Hyflo Supercel (315 kg). The filtrate (pH 7.85) was adjusted to pH 9 with 25% sodium hydroxide, and the resulting solution was extracted twice with 0.5 volumes (2,255 L) of ethyl acetate. The ethyl acetate extracts were combined and concentrated.

The residue obtained was dissolved in toluene (10 mL) and applied to a column containing 60 L of silica gel (Woelm, 100–200 μm), packed in toluene. The column was washed sequentially with 120 L each of toluene and toluene:ethyl acetate (1:1) collecting 25-L fractions. Elution was monitored by bioassay. A80509 was eluted with ethyl acetate. Fractions containing A80509 were combined and concentrated under vacuum to a volume of 20 L.

EXAMPLE 4

Isolation of A80509

A portion of A80509 concentrate (200 mL), obtained as described in Example 3, was dried on silica gel (150 mL) in vacuo and applied to a 7−×60-cm glass column containing 2 L of silica gel (Woelm, 100–200 μm). The column was washed sequentially with 4 L each of and toluene:ethyl acetate (1:1) to remove impurities, collecting 500-mL fractions. Elution was monitored by *Bacillus subtilis* bioassay. A80509 was eluted with ethyl acetate. Fractions containing A80509 were combined and concentrated in vacuo to a residue. The residue was dissolved in a small volume of dioxane and freeze-dried to give 11.7 g of semi-purified A80509.

EXAMPLE 5

Purification of A80509 (Large Scale)

Semi-purified A80509 (300 mg), obtained as described in Example 4, was dissolved in MeOH (10 mL) and applied to a 1"×26" stainless steel column containing 250 mL of silica gel (Whatman LP-1/$C_{18}$) equilibrated in acetonitrile:water (65:35). The column was developed under pressure at a flow rate of 10 mL/min., collecting 25-mL fractions. Elution was monitored by a UV detector at 254 nm. Fractions were assayed by analytical HPLC. Fractions containing A80509 were combined and concentrated in vacuo to a residue. The residue was dissolved in dioxane and lyophilized to give 172.4 mg of purified A80509 (mp 147°–148° C.).

EXAMPLE 6

Chromatographic Identification of A80509

| Chromatographic Identification of A80509 | |
|---|---|
| I. TLC | |
| Absorbent: Silica gel plates (Merck) | |
| Detection: Bacillus subtilis | |
| System | Rf |
| EtOAc:MeOH:7.25N NH₄OH (84:14:2) | 0.51 |
| EtOAc:EtOH (20:1) | 0.48 |
| EtOAc | 0.76 |
| EtOAc:toluene (10:1) | 0.56 |
| II. HPLC | |
| Support: Zorbax C18 | |
| Solvent system: acetonitrile:H₂O (65:35) containing 0.2% H₃PO₄ | |
| Detection: UV at 210 nm | |
| Flow rate: 1.5 mL/min | |
| Retention time: 5.08 min | |
| III. Paper Chromatography | |
| Absorbent: Whatman paper | |
| Detection: *Bacillus subtilis* | |
| System | Rf |
| PrOH:H₂O (1:9) | 0.87 |
| BuOH:EtOH:H₂O (13.5:15:150) | 0.91 |
| Toluene | 0.00 (no movement) |
| 0.06M (NH₄)₂HPO₄*:MeOH: Acetone (12:3:1) | 0.70 |

*pH 7.1

EXAMPLE 7

A80509 Modified Chick Ration

A balanced, high-energy ration adapted to feed chicks for rapid weight gain is prepared by the following recipe:

| Ingredient | % | lbs |
|---|---|---|
| Ground yellow corn | 50 | 1,000 |
| Soybean meal, solvent-extracted dehulled, finely ground, 50 percent protein | 31.09 | 621.8 |
| Animal fat (beef tallow) | 6.5 | 130 |
| Dried fish meal, with solubles (60% protein) | 5.0 | 100 |
| Distillers' solubles from corn | 4.0 | 80 |
| Dicalcium phosphate, feed grade | 1.8 | 36 |
| Calcium carbonate | 0.8 | 16 |
| Vitamin premix (representing vitamins A, D, E, K, and B₁₂, choline, niacin, pantothenic acid, riboflavin, biotin, with glucose bulking agent) | 0.5 | 10 |
| Trace mineral premix (representing MnSO₄, ZnO, KI FeSO₄, CaCO₃) | 0.2 | 4 |
| 2-Amino-4-hydroxybutyric acid (hyroxy analog of methionine) | 0.1 | 2 |
| A80509 (Na Salt) | 0.01 | 0.2 |

These substances are mixed in accordance with standard feed-mixing techniques. Chicks are fed such a ration with water ad libitum.

EXAMPLE 8

A80509-Improved Beef-Cattle Ration

A balanced high-grain beef-cattle ration is prepared as follows:

| Ingredient | % | lbs |
|---|---|---|
| Finely ground corn | 67.8 | 1356 |
| Ground corn cob | 10 | 200 |
| Dehydrated alfalfa meal, 17 percent protein | 5 | 100 |
| Dehulled soybean meal, solvent extracted, 50 percent protein | 9.9956 | 199.912 |
| Cane molasses | 5 | 100.0 |
| Urea | 0.6 | 12.0 |
| A80509 (free base) | 0.0044 | 0.088 |
| Dicalcium phosphate, feed grade | 0.5 | 10.0 |
| Calcium carbonate | 0.5 | 10.0 |
| Sodium chloride | 0.3 | 6.0 |
| Trace mineral premix | 0.03 | 0.6 |
| Vitamin A and D₂ premix* | 0.07 | 1.4 |
| Vitamin E premix** | 0.05 | 1.0 |
| Calcium propionate | 0.15 | 3.0 |

*Containing per pound: 2,000,000 I.U. of vitamin A; 227,200 I.U. of vitamin D₂ and 385.7 g of soybean feed with 1% oil added
**Corn distillers dried grains with solubles containing 20,000 I.U. of d-alpha-tocopheryl acetate per pound The mixed feed is compressed into pellets. At an average daily ingestion rate of 15 pounds of feed per animal, this feed supplies approximately 300 mg of A80509 per animal per day.

We claim:

1. Antibiotic A80509 which has the following characteristics

State: white amorphous powder (lyophilized)
Mp: 147°-148° C.
pKa: =6.7 (66% aqueous dimethylformamide)
$[\alpha]^{25}D$: +35.1° (c 10, MeOH) Mol. wt.: 856 (field desorption and fast atom bombardment mass spectrometry)
Empirical formula: $C_{42}H_{57}N_6O_9ClS$
UV (EtOH): 336 nm ($\epsilon$5,070); acid—241 ($\epsilon$12,600) and 311 ($\epsilon$4,750)
IR (CHCl₃) See FIG. 1; or a or salt of A80509.

2. A compound of claim 1 which is A80509 or a pharmaceutically acceptable salt of A80509.

3. A method for increasing feed efficiency in animals which comprises orally administering to the animal an effective feed-efficiency increasing amount of a compound of claim 2.

4. A feed composition for increasing feed efficiency in animals comprising animal feed and an effective feed-efficiency-increasing amount of a compound of claim 2.

5. A method for improving weight gains in animals which comprises administering to the animal an amount of a compound of claim 2 which increases weight gains.

6. A composition for increasing weight gains in animals comprising an effective amount of a compound of claim 2 for increasing weight grains and a pharmaceutically acceptable carrier.

7. A process for producing antibiotic A80509, as defined in claim 1, which comprises cultivating *Streptomyces mutabilis* NRRL 18269, or an A80509-producing nutant thereof, in a culture medium containing assimilable sources of carbon, nitrogen, and inorganic salts under submerged aerobic fermentation conditions until a sufficient amount of antibiotic A80509 is produced.

8. The process of claim 7 which includes the additional step of separating A80509 from the culture medium.

9. The process of claim 7 wherein S. mutabilis NRRL 18269 is used.

* * * * *